(12) United States Patent
Barcelo et al.

(10) Patent No.: US 10,828,637 B2
(45) Date of Patent: Nov. 10, 2020

(54) MICROFLUIDIC CHIP WITH ANCHORED NANO PARTICLE ASSEMBLY

(71) Applicant: Hewlett-Packard Development Company, L.P., Houston, TX (US)

(72) Inventors: Steven Barcelo, Palo Alto, CA (US); Anita Rogacs, San Diego, CA (US); Viktor Shkolnikov, Palo Alto, CA (US); Milo Overbay, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 318 days.

(21) Appl. No.: 15/792,732

(22) Filed: Oct. 24, 2017

(65) Prior Publication Data

US 2019/0022650 A1 Jan. 24, 2019

Related U.S. Application Data

(63) Continuation-in-part of application No. PCT/US2017/042871, filed on Jul. 19, 2017.

(51) Int. Cl.
*B01L 3/00* (2006.01)
*G01N 21/64* (2006.01)
(Continued)

(52) U.S. Cl.
CPC ........ *B01L 3/502738* (2013.01); *A61K 49/00* (2013.01); *B01L 3/502707* (2013.01);
(Continued)

(58) Field of Classification Search
CPC .................. G01N 21/78; G01N 33/84; G01N 2021/7759; G01N 2021/651; G01N 21/658; G01N 21/6428; G01N 21/6486; G01N 2021/6439; B05D 1/18; B01L 3/502738; B01L 3/502707; B01L 3/502715; B01L 9/527; B01L 2200/0647; B01L 2400/0433;
(Continued)

(56) References Cited

U.S. PATENT DOCUMENTS 7,776,425 B2 8/2010 Kalkan
7,871,570 B2 1/2011 Huang et al.
(Continued)

FOREIGN PATENT DOCUMENTS

CN 103409734 A 11/2013
CN 104359893 A 2/2015
(Continued)

OTHER PUBLICATIONS

Chang H. Lee, Plasmonic Paper as a Highly Efficient SERS Substrate, Army Research Laboratory (Sep. 2012).
Wang, Y. et al., Fabrication of Patternable Nanopillars for Microfluidic Sers Devices Based on Gap-induced Uneven Etching (Jan. 2015). http://ieeexplore.ieee.org/document/7050953/.

*Primary Examiner* — Dennis White
(74) *Attorney, Agent, or Firm* — Rathe Lindenbaum LLP (57) ABSTRACT

A microfluidic chip may include a substrate, chamber supported by the substrate, a sacrificial material in the chamber, a spectroscopically active nano particle assembly anchored within the chamber by the sacrificial material and a fluid supply port connected to the chamber. Each spectroscopically active nano particle assembly may include a cluster of nanoparticles.

20 Claims, 8 Drawing Sheets

(51) Int. Cl.
    *B29C 39/00*        (2006.01)
    *B01L 9/00*         (2006.01)
    *A61K 49/00*        (2006.01)
    *G01N 21/65*        (2006.01)

(52) U.S. Cl.
    CPC ......... B01L 3/502715 (2013.01); B01L 9/527 (2013.01); B29C 39/006 (2013.01); G01N 21/6428 (2013.01); G01N 21/6486 (2013.01); B01L 3/502761 (2013.01); B01L 2200/0647 (2013.01); B01L 2200/16 (2013.01); B01L 2300/0816 (2013.01); B01L 2300/0867 (2013.01); B01L 2400/0433 (2013.01); B01L 2400/0442 (2013.01); G01N 21/658 (2013.01); G01N 2021/6439 (2013.01); G01N 2021/651 (2013.01)

(58) Field of Classification Search
    CPC ....... B01L 3/502761; B01L 2300/0816; B01L 2400/0442; B01L 2200/16; B01L 2300/0867; A61K 49/00; B29C 39/006
    See application file for complete search history.

(56) References Cited

U.S. PATENT DOCUMENTS

| | | | |
|---|---|---|---|
| 8,687,186 | B2 | 4/2014 | Wang |
| 9,274,058 | B2 | 3/2016 | Li et al. |
| 9,719,926 | B2 | 8/2017 | Astier et al. |
| 2011/0165077 | A1 | 7/2011 | Qian |
| 2013/0021605 | A1* | 1/2013 | Yi ................. G01N 21/658 356/301 |
| 2013/0107254 | A1 | 5/2013 | Yu |
| 2014/0209837 | A1* | 7/2014 | Barcelo ........... G01N 21/658 252/408.1 |
| 2015/0253321 | A1 | 9/2015 | Chou et al. |
| 2017/0167981 | A1 | 6/2017 | Hu et al. |

FOREIGN PATENT DOCUMENTS

| | | |
|---|---|---|
| CN | 106669872 | 5/2017 |
| WO | WO-2010073260 | 7/2010 |
| WO | WO-2013185167 | 12/2013 |
| WO | WO-2016195389 | 12/2016 |

\* cited by examiner

MICROFLUIDIC CHIP WITH ANCHORED NANO PARTICLE ASSEMBLY

CROSS REFERENCE TO RELATED APPLICATION

The present application claims priority under 35 USC 119 from co-pending PCT patent application PCT/US2017/042871 filed Jul. 19, 2017 and entitled PROTECTED NANO-PARTICLE ASSEMBLIES, the full disclosure of which is hereby incorporated by reference.

BACKGROUND

Spectroscopic tagging may use emissive nano particles that attach to or that react with a target. These may be used for identification purposes, tracking purposes, in-vivo analyses, and the like. For example, emissive particles based on Surface Enhanced Raman Spectroscopy (SERS) may be used for tagging in biological systems, such as reacting with bacteria, proteins, DNA, and the like, to allow the determination of presence and concentration.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION OF EXAMPLES

Disclosed herein are example microfluidic chips and methods that facilitate stable storage and compact preparation of spectroscopic tagging solutions. Disclosed herein are example microfluidic chips and methods that anchor spectroscopically active nano particle assemblies which may be dis-anchored or released when the microfluidic chip is to be used. The example microfluidic chips and methods may store the anchored spectroscopically active nano particle assemblies in a dry state, within a dry chamber, wherein subsequent addition of a fluid through a fluid supply port dis-anchors the assemblies and releases them for use. In some implementations, the microfluidic chips facilitate selective forming of nano particle assembly with selected reporter molecules and/or selected functionalization.

Disclosed herein is an example microfluidic chip that may comprise a chamber, a sacrificial material in the chamber, a spectroscopically active nano particle assembly anchored within the chamber by the sacrificial material and a fluid supply port connected to the chamber. Each spectroscopically active nano particle assembly may include a cluster of nanoparticles.

Disclosed herein is an example microfluidic chip that may comprise a chamber, a layer of sacrificial material in the chamber and spectroscopically active nano particle assemblies anchored by the layer within the chamber. Microfluidic chip may further comprise a solvent supply passage connected to the chamber, a discharge passage extending from the chamber and a reagent supply passage connected to the discharge passage.

Disclosed herein is an example method for forming a spectroscopic tagging solution preparation microfluidic chip. The method may comprise forming a chamber and a fluid supply port connected to the chamber in at least one layer of the microfluidic chip. The method may further comprise anchoring a spectroscopically active nano particle assembly in the chamber, wherein the chamber is devoid of fluid.

Disclosed herein is an example method for preparing a spectroscopic tagging solution on a microfluidic chip. The method may comprise supplying fluid to a chamber in which a spectroscopically active nano particle assemblies anchored. The method may further comprise dis-anchoring the spectroscopically active nano particle assembly such that the nano particle assembly become suspended in the fluid.

As will be appreciated, examples provided herein may be formed by performing various microfabrication and/or micromachining processes on a substrate to form and/or connect structures and/or components. The substrate may comprise a silicon based wafer or other such similar materials used for microfabricated devices (e.g., glass, gallium arsenide, plastics, etc.). Examples may comprise microfluidic channels, fluid actuators, and/or volumetric chambers. Microfluidic channels and/or chambers may be formed by performing etching, microfabrication processes (e.g., photolithography), or micromachining processes in a substrate. Accordingly, microfluidic channels and/or chambers may be defined by surfaces fabricated in the substrate of a microfluidic device. In some implementations, microfluidic channels and/or chambers may be formed by an overall package, wherein multiple connected package components that combine to form or define the microfluidic channel and/or chamber.

In some examples described herein, at least one dimension of a microfluidic channel and/or capillary chamber may be of sufficiently small size (e.g., of nanometer sized scale, micrometer sized scale, millimeter sized scale, etc.) to facilitate pumping of small volumes of fluid (e.g., picoliter scale, nanoliter scale, microliter scale, milliliter scale, etc.). For example, some microfluidic channels or passages may facilitate capillary pumping due to capillary force. In addition, examples may couple at least two microfluidic channels to a microfluidic output channel via a fluid junction.

Figure 1:
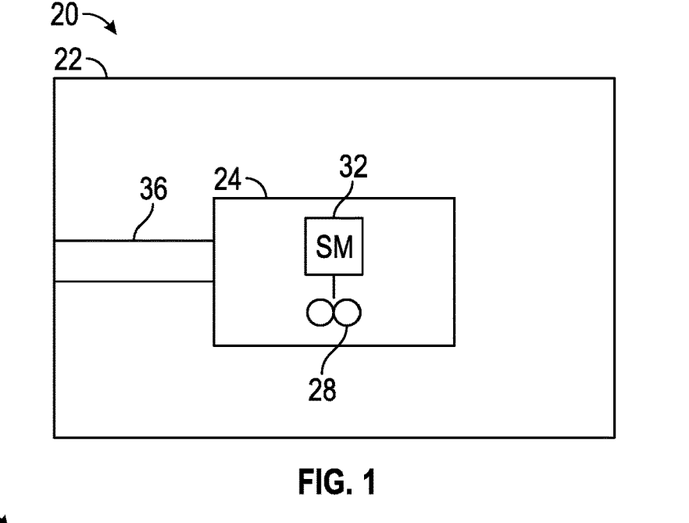
FIG. 1 is a schematic diagram illustrating portions of an example microfluidic chip with an example anchored spectroscopic nano particle assembly.

FIG. 1 schematically illustrates portions of an example microfluidic chip 20 that comprises integrated nano particle assemblies. Microfluidic chip 20 anchors spectroscopically active nano particle assemblies which may be dis-anchored or released when the microfluidic chip 20 is to be used. Microfluidic chip 20 may store the anchored spectroscopically active nano particle assemblies in a dry state, within a dry chamber, wherein subsequent addition of a fluid through a fluid supply port dis-anchors the assemblies and readies the nano particle assemblies for use. Microfluidic chip 20 facilitates automated preparation of the nano particle assemblies.

As shown by FIG. 1, microfluidic chip 20 comprises die or substrate 22, chamber 24, spectroscopically active nano particle assembly 28, sacrificial material 32 and fluid supply port 36. Die or substrate 22 forms a base or platform for microfluidic chip 20. Substrate 22 may be formed from silicon, glass, quartz, silicon nitride, sapphire, aluminum oxide, diamond, diamond-like carbon, or other rigid inorganic materials, such as metals and metallic alloys. In some implementations, substrate 22 may be a polymeric material such as a polyacrylate, a polyamide, a polyolefin such as polyethylene polypropylene or a cyclic olefin, polyethylene naphthalate, or other polymeric material suitable for making films. Any of such polymeric materials may be a copolymer, homopolymer or a combination thereof. In some implementations, substrate 22 may be a web use in a roll-to-roll fabrication process.

Chamber 24 comprises an internal cavity or an internal volume formed within or supported by substrate 22. Chamber 24 contains at least one spectroscopically active nano particle assembly 28. Chamber 24 provides a volume by which nano particle assembly 28 may be exposed to a fluid when dis-anchored within the chamber, facilitating suspension of the nano particle assembly 28 within the fluid. Although illustrated as being rectangular, chamber 24 may have any of a variety of different sizes and different shapes. In some implementations, chamber 24 may be part of a microfluidic passage leading to a destination.

Spectroscopically active nano particle assembly 28 comprises a cluster or grouping of individual nanoparticles providing plasmonically active surfaces. The plasmonic active surfaces may comprise a metal. For example, the plasmonically active surfaces of the individual particles may comprise noble metals, such as ruthenium (Ru), rhodium (Rh), palladium (Pd), silver (Ag), osmium (Os), iridium (Ir), platinum (Pt), and gold (Au), as well as copper, or alloys thereof. Other metals may be used to provide the plasmonic surfaces, such as aluminum (Al), titanium (Ti), or other metals.

Although each assembly 28 is illustrated as comprising a pair of adjacent nanoparticles, in other implementations, each assembly 28 may comprise other numbers of nanoparticles assembled or held adjacent to one another. For example, assembly 28 may comprise a trimer, tetramer, or pentamer. Junctions between the nanoparticles of the assembly 28 form at least one "hot spot".

In some implementations, at least one reporter molecule (sometimes referred to as a spectroscopic tag) may be captured or trapped in the junctions, wherein the reporter molecule emits a signature radiation pattern, which is enhanced as a result of the molecule being captured in the hotspot. The reporter molecules may be any number of molecules that give a spectroscopic response, for example, in a surface enhanced luminescence technique. For use in surface enhanced Ramen spectroscopy (SERS), the reporter molecule may be trans-1,2-bis (4-pyridyl) ethylene. However, any number of other reporter molecules may be used depending on the spectroscopic techniques.

As will be described hereafter, in some implementations, each nano particle assembly 28 may additionally be functionalized using molecules with the binding agent on one end and a functional group on the other end. For example, the binding agent may include thiols for binding to the exposed portion of the plasmonic surface of the assembly 28. The functional group may be designed to promote stability in solution, bind to specific substrates or tissues, or both. One example of a functional group may be a monoclonal antibody selected to bind to an express group on the surface of a cell. The functional group may comprise a short DNA segment that is to bind to a complementary DNA segment. A functional group may comprise a long paraffinic chain that stabilizes the nano particle assembly 28 in organic materials, such as solvents, fatty acids, triglycerides and the like.

In some implementations, the functional group may be a therapeutic agent. For example, therapeutic agent may be released when the nano particle assembly 28 is exposed to an excitation source. In such an implementation, the functional group may facilitate the delivery of local therapeutics with a plasmonic the activated drug delivery system using nano particle assembly 28.

In some implementations, nano particle assembly 28 may be tuned to specific applications. For example, in some implementations, the size and/or geometry of nano particle assembly 28 may be customized for a particular application such as where the nano particle assembly 28 is intended to bind to a particular substrate or tissue, where the nano particle assembly 28 is to pass through cell walls or where the nano particle assembly 28 is to be utilized in solution.

In some implementations, the nano particle assembly 28 may be encapsulated or covered with a protective outer coating that may protect any reporter molecules or stabilize the assembly 28 in solution. For example, the protective coating may promote stability of a suspension or block further aggregation of the nano particle assembly 28. Examples of such a coating include, but are not limited to, silicon dioxide, metal oxides, metal carbides, metal sulfide, diamond, spinel structures ($MgAl_2O_4$) and the like. Protective coating may be applied using a vapor deposition technique, atomic layer deposition or liquid deposition techniques.

Sacrificial material 32 comprises a material that anchors nano particle assembly 28 within chamber 24. In one implementation, sacrificial material 32 comprises a column, pillar or the like that is sandwiched between nano particle assembly 28 and an internal surface of chamber 24. In another implementation, sacrificial material 32 comprises a layer on the internal surface of chamber 24 and which at least partially encapsulates nano particle assembly 28.

In one implementation, sacrificial material 32 has a chemical composition and thickness or dimension such that sacrificial material 32 breaks down or dissolves upon exposure to the fluid having a predetermined chemical composition, releasing or dis-anchoring nano particle assembly 28 into the fluid. For example, in one implementation, sacrificial material 32 may comprise aluminum. Examples of other sacrificial materials that may be utilized, depending upon the fluid utilized to dis-anchor the nano particle assembly 28, include, but are not limited to, titanium, chromium, polyimide, poly(methyl methacrylate) or polystyrene.

In other implementations, sacrificial material 32 has a chemical composition and thickness or dimension such that the sacrificial material 32 breaks down and releases nano particle assembly 28 in response to other applied stimulus or excitation. For example, in one implementation, sacrificial material 32 has a chemical composition and thickness such that material 32 breaks down in response to reaching a predetermined temperature or in response to applied electromagnetic radiation in the form of certain optical wavelengths. In such an implementation, the stimulus may be applied while in the fluid such that the released nano particle assemblies 28 become suspended in the fluid. Examples of such sacrificial material 32, include, but are not limited to, poly(methyl methacrylate), polyimide or polystyrene.

Fluid supply port 36 comprise a port through which fluid is supplied into chamber 24. Prior to the receipt of such fluid, chamber 24 may be dry or devoid of fluid. The dry state of chamber 24 and its contents may provide a more stable storage of nano particle assembly 28. Fluid supply port 36 facilitates the supply of fluid for suspending the released nano particle assemblies 28. In one implementation, fluid supply port 36 connects to an external port by which fluid from an external source may be supplied. In another implementation, fluid supply port 36 connects to a fluid reservoir contained on substrate 22 of microfluidic chip 22, wherein fluid supply 22 may be selectively opened or connected to chamber 24, facilitating the flow of the fluid into chamber 24.

Figure 2:
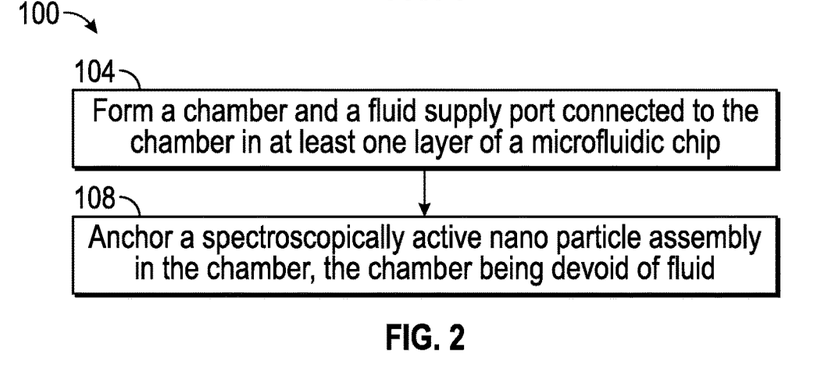
FIG. 2 is a flow diagram of an example method for forming a microfluidic chip having an anchored spectroscopic nano particle assembly.

FIG. 2 is a flow diagram of an example method 100 for forming a microfluidic chip that stores and anchors a spectroscopically active nano particle assembly. Although method 100 is described in the context of forming microfluidic chip 20, it should be appreciative that method 100 may be utilized to form any of the microfluidic chips described hereafter or other similar microfluidic chips.

As indicated by block 104, chamber 24 is formed in a substrate 22 of a microfluidic chip 20. A fluid supply port 36 is also formed. The fluid supply port 36 is connected to the chamber in at least one layer of substrate 22 of the microfluidic chip 20.

As indicated by block 108, a spectroscopically active nano particle assembly, such as nano particle assembly 28, is anchored in the chamber 24. The chamber 24 is devoid of fluid. As described above, the spectroscopically active nano particle assembly may comprise a cluster or grouping of individual nanoparticles having plasmonically active surfaces. The nano particle assembly may additionally comprise at least one reporter molecule captured between the individual nanoparticles, in the "hot spot" of the nano particle assembly. In some implementations, the nano particle assembly may further comprise functionalizing molecules. In some implementations, the various molecules of the assembly may be at least partial encapsulated within a protective coating.

Figure 3:
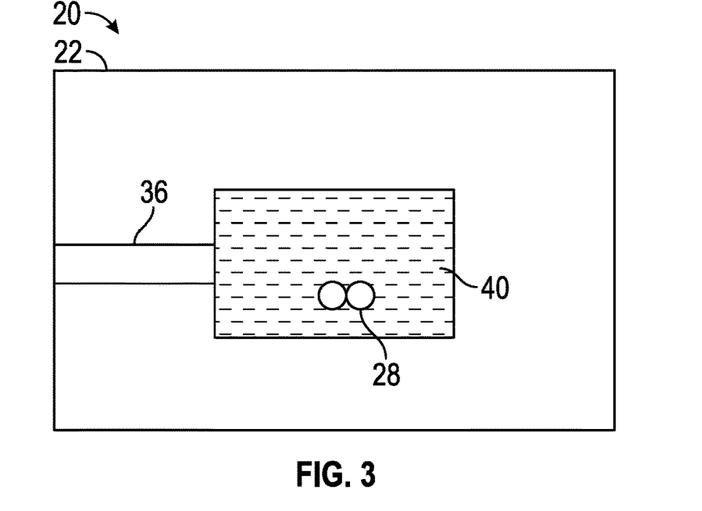
FIG. 3 is a schematic diagram illustrating the microfluidic chip of FIG. 1 after the spectroscopic nano particle assembly has been dis-anchored or released into fluid.

FIG. 3 is a schematic diagram illustrating portions of microfluidic chip 20 during use of microfluidic chip 20. FIG. 3 illustrates microfluidic chip 20 after a fluid has been supplied to chamber 24 through port 36 and after dis-anchoring of nano particle assembly 28. FIG. 3 illustrates chamber 24 containing a fluid 40 and nano particle 28 carried or suspended within fluid 40. In one implementation, sacrificial material 32 has dissolved into fluid 40.

Figure 4:
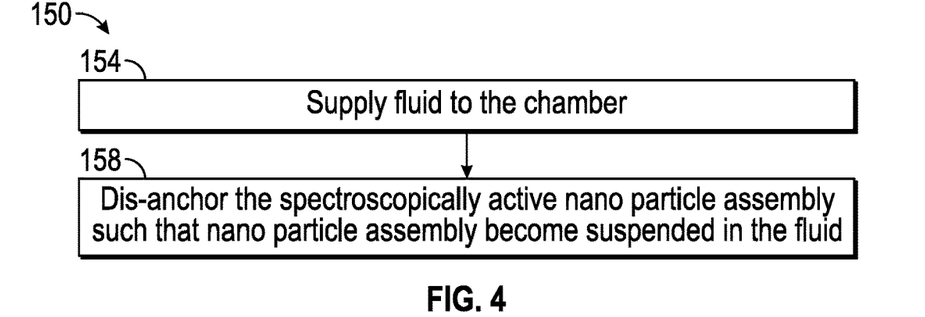
FIG. 4 is a flow diagram of an example method for preparing a spectroscopic tagging solution using the example microfluidic chip of FIG. 1.

FIG. 4 is a flow diagram of an example method 150 for preparing a nano particle assembly tagging solution using a microfluidic chip, such as microfluidic chip 20. As indicated by block 154, fluid 40 is supplied to chamber 24 through port 36. As indicated by block 158, the spectroscopically active nano particle assembly 28 is dis-anchored such that the nano particle assembly 28 become suspended in the fluid 40.

As discussed above, in some implementations, the composition of the sacrificial material 32 and the composition of the fluid 40 may be such that sacrificial material 32 dissolves in the fluid. For example, in some implementations, sacrificial material 32 may dissolve in a weak acid or base so as to release the nano particle assembly 28 into solution. For example, in one implementation, sacrificial material 32 may comprise aluminum which dissolves in fluid 40 in the form of a diluted sodium hydroxide or diluted hydrogen chloride. In another implementation, sacrificial layer may be formed from Poly(methyl methacrylate) (PMMA), also known as acrylic or acrylic glass, wherein the sacrificial layer 32 is dissolvable in a fluid such as acetone. In other implementations, sacrificial material 32 may breakdown in response to other applied stimulus such as heat or light, wherein the nano particle assembly 28 is released into fluid 40.

Figure 5:
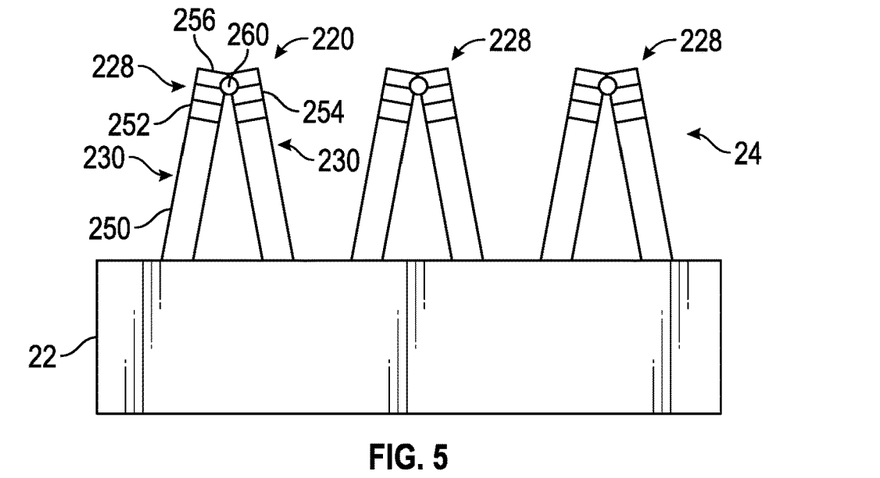
FIG. 5 is a side view of a portion of an example microfluidic chip with example anchored spectroscopic nano particle assemblies.

FIG. 5 is a side view illustrating portions of microfluidic chip 220, an example implementation of microfluidic chip 20 described above. Microfluidic chip 220 is similar to microfluidic chip 20 except that microfluidic chip 220 comprises nano particle assemblies 228 which are as part of a cluster of at least two closed nano pillars 230 which anchor the nano particle assembly 228 within chamber 24, to the floor of chamber 24 provided by substrate 22. FIG. 5 illustrates microfluidic chip 220 in a stored state, during which nano particle assembly 228 are anchored and while chamber 24 is devoid of fluid.

As shown by FIG. 5, each nano pillar 230, sometimes referred to as a nano finger, comprises post 250, sacrificial layer 252, plasmonic cap 254, and cover layer 256. Post 250 supports sacrificial layer 252, plasmonic caps 254 and cover layer 256. Posts 250 are bendable or closable towards one another, such as in response to capillary forces. In one implementation, such posts 250 have an aspect ratio of and at least 10:1 (a height of at least 10 times the thickness or diameter). In one implementation, such posts have a thickness or diameter between 50 nm and 150 nm, while, at the same time, having a height of at least 500 nm and, in one implementation, at least 700 nm. In some implementations, the posts 250 are movable and are self-actuating, wherein such columnar structures bend or flex towards one another in response to micro-capillary forces so as to self-organize, wherein such bending facilitates close spacing between the structures for greater scattered radiation intensity.

The polymer material from which posts 250 are formed facilitates the use of molding, imprinting or other fabrication techniques to form posts 250. The polymer material further facilitates bending and flexing of posts 250 and subsequent closing to form the nano particle assemblies 228. Examples of polymer materials from which each post 250 may be formed include, but are not limited to, photo resists, hard mold resins such as PMMA, soft mold polymers such as PDMS, ETFE or PTFE, hybrid-mold cross-linked uv-curable or thermal-curable polymers based on acrylate, methacrylate, vinyl, epoxy, siloxane, peroxide, urethane or isocyanate. The polymer materials may be modified to improve imprint and mechanical properties with copolymers, additives, fillers, modifiers, photoinitiators and the like.

Sacrificial layer 252 extends between post 250 and metallic caps 254. Sacrificial layer 252 anchors metallic cap 254 to post 250 within chamber 24. Sacrificial layer 252 facilitates the subsequent separation of metallic caps 254 from posts 250. In one implementation, sacrificial layer 252 is formed from a metal that is dissolvable in a fluid. In one implementation, sacrificial layer 252 may be formed from aluminum. In another implementation, sacrificial layer 252 may be formed from PMMA which is dissolvable in acetone.

Each metallic cap 254 comprises a metallic structure formed on top of posts 230. Each metallic cap 254 comprises a metal material that forms a plasmonic surface that enhances the intensity of electromagnetic radiation emitted as a result of the reaction of the analyte and the light impinging the reporter or tag molecule. In one implementation, each metallic cap 254 may be formed from a metal and provides a plasmonic surface on each of nano pillars 230. Metallic cap 254 may comprise noble metals, such as ruthenium (Ru), rhodium (Rh), palladium (Pd), silver (Ag), osmium (Os), iridium (Ir), platinum (Pt), and gold (Au), as well as copper, or alloys thereof. Other metals may be used provide the plasmonic cap 254, such as aluminum (Al), titanium (Ti), or other metals.

Cover layer 256 comprises a layer of material formed on top of metallic cap 254. In one implementation, cover layer 256 comprises a material forming sacrificial layer 252 such that metallic cap 254 are sandwiched between two layers 252, 256. Cover layer 256 inhibits the agglomeration of the subsequent formed nano particle assemblies 228. In some implementations, cover layer 256 may further facilitate functionalization of the subsequent formed nano particle assembly 228. In yet other implementations, cover layer 256 may be omitted.

As further shown by 5, the array of nano pillars 230 are closed such that metallic caps 254 are drawn into close proximity with one another, capturing or trapping at least one reporter or tag molecule 260 therebetween. The reporter molecules 260 may be any number of molecules that give a spectroscopic response, for example, in a surface enhanced luminescence technique. For use in SERS, the reporter molecule may be trans-1,2-bis (4-pyridyl) ethylene. However, any number of other reporter molecules may be used depending on the spectroscopic techniques.

In one implementation, nano pillars 230 are arranged in clusters or groups, wherein each of the nano pillars of the cluster group are drawn towards one another, capturing reporter molecule 260 in a hotspot at the juncture of the nano pillars 230. In one implementation, nano pillars 230 are arranged in pentamers, clusters of five nano pillars 230 that close towards one another. In other implementations, nano pillars 230 are arranged in other groupings, such as a dimer (two closed nano pillars), trimer (three closed nano pillars) or tetramer (five close nano pillars). The metallic caps 254 of nano pillars 230 which have closed into close proximity with one another, and the captured reporter molecule 260, form an individual nano particle assembly 228. This nano particle assembly 228 remains anchored within chamber 24 by posts 250 and sacrificial material 252.

Figure 6:
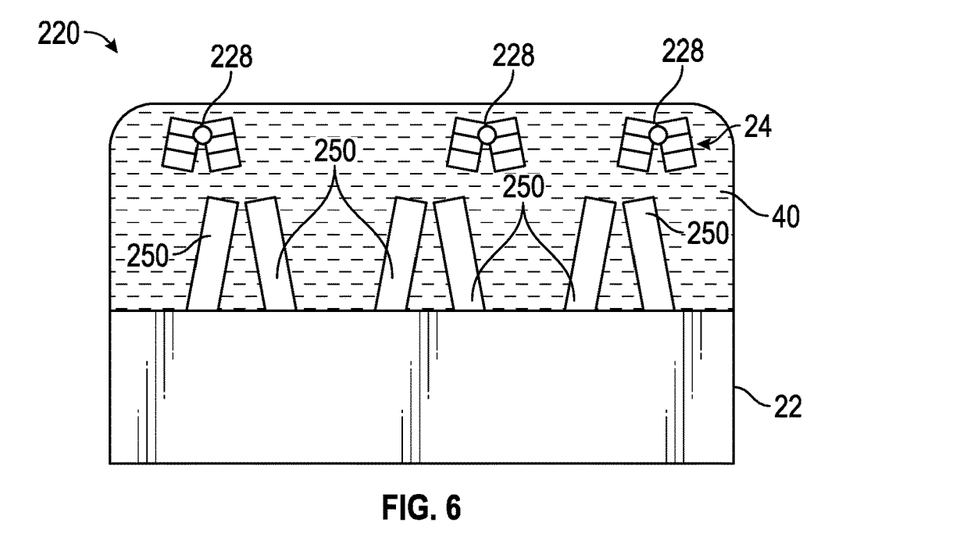
FIG. 6 is a side view of the example microfluidic chip of FIG. 5 following dis-anchoring of the example spectroscopic nano particle assemblies in fluid.

FIG. 6 illustrates the release of or dis-anchoring of the individual nano particle assemblies 228. As shown by FIG. 6, while being exposed to fluid 40, nano particle assemblies 228 are released and become suspended within fluid 40. In one implementation, sacrificial material 252 is formed from a material that dissolves in fluid 40, wherein nano particle assemblies 228 become suspended in the fluid 40. In one implementation, sacrificial material 252 may comprise aluminum. In another implementation, sacrificial material 252 may comprise PMMA dissolved in a fluid 40, such as acetone.

Figure 7:
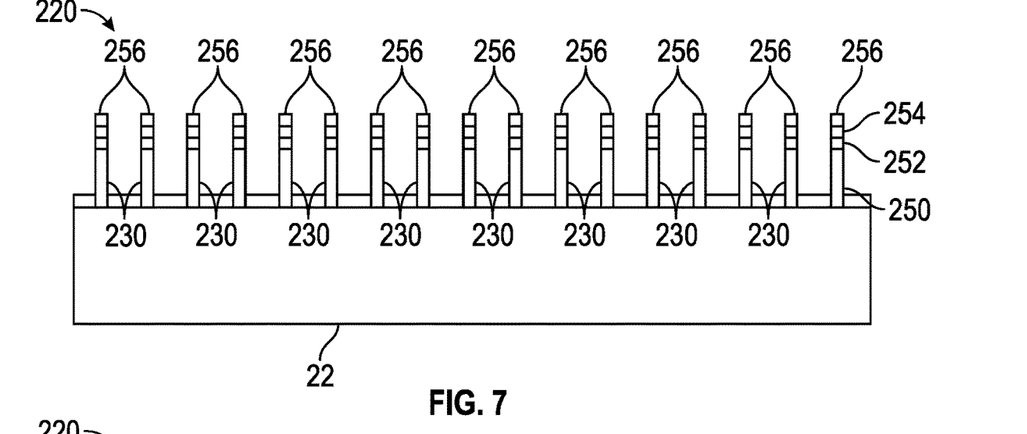
FIG. 7 is a side view schematically illustrating nano pillars supporting individual nanoparticles for forming spectroscopic nano particle assemblies.
Figure 8:
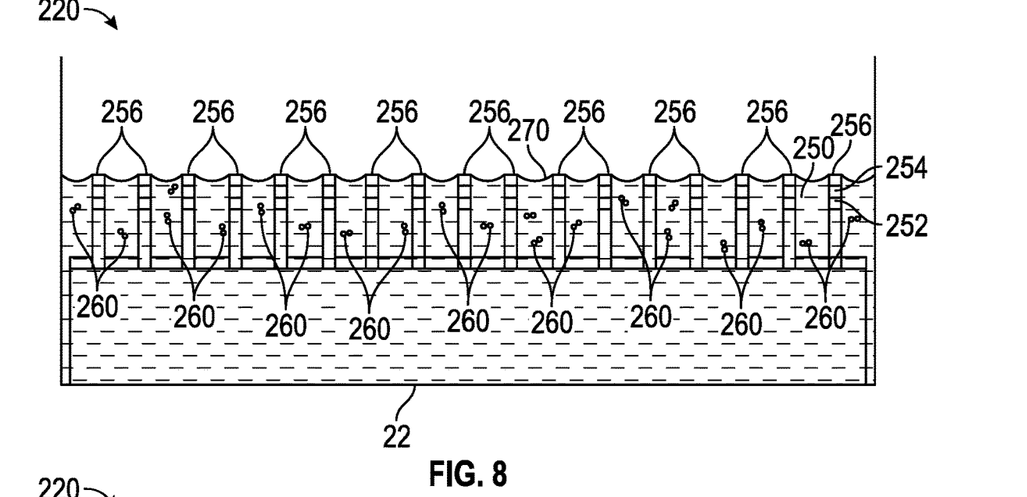
FIG. 8 is a side view schematically illustrating the nano pillars immersed in a fluid containing reporter molecules.
Figure 9:
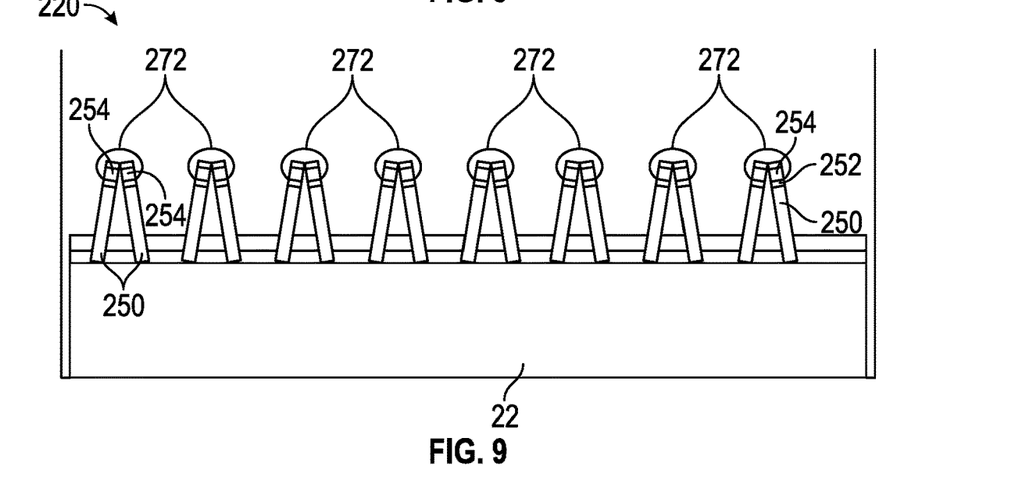
FIG. 9 is a side view schematically illustrating evaporation of the fluid and closure of the nano pillars to capture the reporter molecules and form the example anchored spectroscopic nano particle assemblies of FIG. 5.

FIGS. 7-9 illustrate one example method of forming nano particle assemblies 228 as part of nano pillars 230 shown in FIG. 5. As shown by FIG. 7, flexible nanopillars 204 are formed on the surface of the substrate 22. Posts 250 may be formed by any number processes, including nano-embossing, lithography followed by reactive ion etching or chemical etching, UV or thermal curing, and the like. In a nano-embossing process, a layer of material may be softened and then run through a die to form the flexible post 250 column of material.

In some examples, the posts 250 may be deposited on the substrate 22, for example, using nano-printing, ion deposition techniques, and the like. In a nano-printing process, the materials forming the flexible post 250 may be directly deposited, or printed, on the surface of the substrate 22. In other examples, nano-wires may be grown on the substrate through ion deposition. In growing the nano-wires to produce the flexible column, nano-wire seeds may be deposited onto the substrate 22. In some examples, the nano-wire seeds may be silicon nano-structures, and the nano-wires may be silicon dioxide structures grown during chemical vapor deposition from silane.

Sacrificial material 252 is formed as a layer upon pillars 250. In one implementation, the sacrificial material 252 may be deposited using a thin-film vacuum-apparatus to deposit the sacrificial material on post 250. The sacrificial material may be deposited at an angle of about 30° to a surface of the substrate 22 to enhance formation of the sacrificial material 252, while decreasing the amount of sacrificial material deposited in other locations.

In other implementations, the sacrificial material 252 may be deposited as a layer upon a layer that is to form post 250. Thereafter, selective material removal or material forming techniques are applied to both layers to form post 250 with the overlying sacrificial material 252. For example, nano-embossing, lithography followed by reactive ion etching or chemical etching, UV or thermal curing, and the like may be applied to the layers.

Once the flexible posts 250 and the overlying sacrificial material 252 are formed, metal caps 254 may be formed over the nanopillars. The metal caps 254 may be deposited using a thin-film vacuum-apparatus to deposit metal onto the sacrificial material 252. The metal may be deposited at an angle of about 30° to a surface of the substrate 22 to enhance formation of the metal caps 254, while decreasing the amount of metal deposited in other locations. The material deposited from the metallic vapor may also be limited to control the deposition, and lower the amount deposited on the substrate 22 or on sides of the post 250.

Other techniques may be used to form the metal caps 254. In some examples, the substrate 22 including the flexible post 250 and sacrificial material 252 may be immersed in a plating solution that includes metal cations. An electric potential applied to the substrate 22 may cause deposition of metal at the top of the sacrificial material 252, as the top of the sacrificial material 252 may have a more concentrated or enhanced electrical field. The metal caps 254 may be precipitated from colloidal suspensions of metallic nanoparticles when an electric potential is applied to the substrate 22. Any number of other techniques may be used to form the metal caps 254.

Thereafter, cover layer 256 is formed upon metallic caps 254. Cover layer 256 may be formed upon metallic caps 254 in the same manner as sacrificial material 252 was formed upon post 250. In one implementation, cover letter 256 may be deposited using a thin-film vacuum-apparatus to deposit the cover layer 256 on 248. The cover layer 256 may be deposited at an angle of about 30° to a surface of the substrate 22 to enhance formation of the cover layer 256, while decreasing the amount of the material of cover layer 256 deposited in other locations.

FIGS. 8 and 9 illustrate the absorption of the reporter molecule 260 on the metallic caps 254. As shown by FIG. 8, the nano pillars are submersed in a fluid 270 containing the reporter molecules 260. As shown by FIG. 9, the fluid 270 is subsequently evaporated. Evaporation of the fluid 270 provides increased microcapillary pressure around the flexible nanopillars 230. This causes flexible nanopillars 230 to collapse, bringing the metal caps 254 of adjacent flexible nanopillars 230 together, forming a cluster of metallic nano-particles attached to the flexible posts of the flexible nanopillars. In some examples, the fluid 270 with the reporter molecules 260 may be incubated before the evaporation to allow reactions before the evaporation.

Multiple fluids may be used in the preparation. For example, the reporter molecules 260 may be dissolved in a first fluid and the flexible nanopillars 230 and metal caps 254 may be incubated to allow reaction. A clean fluid may be used to rinse the surface to eliminate excess reporter molecules 260. The same fluid or another fluid may then be evaporated from the surface to collapse the nanopillars 230. Reporter molecules 260 do not have to be added by dissolution in the fluid 270. In some examples, the metal caps 254 of the flexible pillars 230 may be reacted with gas phase reporter molecules after which a fluid 270 may be used to collapse the flexible nanopillars 230.

FIG. 9 illustrates an example of collapsed groups 272 formed by the evaporation of the fluid 270. The reporter molecules 260 may be adsorbed on the surfaces of the metal caps 254, or may be trapped in the nm-scale gaps between the metal caps 254. The number of metal caps 254 in each collapsed group of nano pillars 230 may vary depending on the dynamics of the collapse process. For example, a collapsed group 254 may include a cluster of metallic nano-particles formed from two metal caps 254, three metal caps 254, four metal caps 254, or five metal caps 254, or more. The pentamer shape, formed from five metal caps 254, has been shown to have particularly good performance on a substrate and may also perform well in solution due to the large number of dipole axes.

Figure 10:
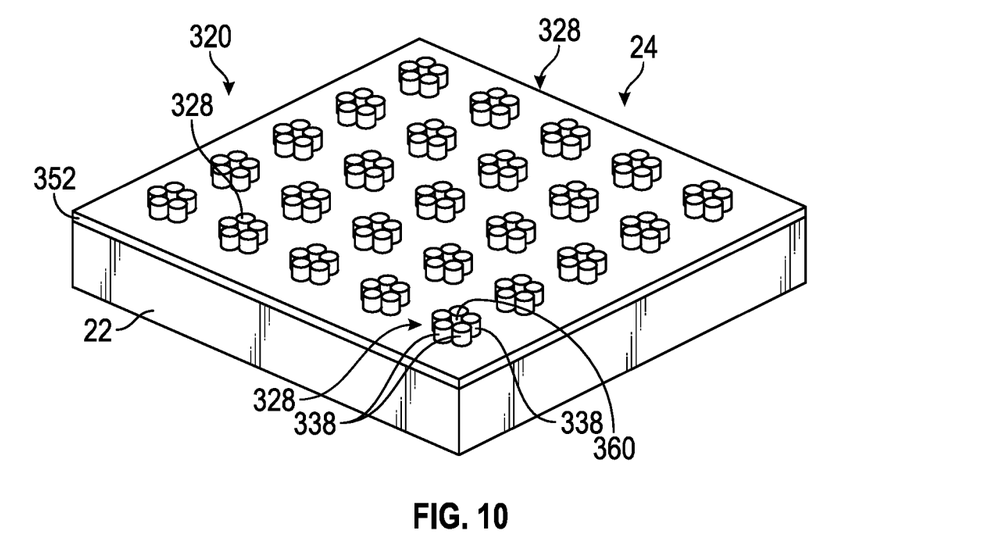
FIG. 10 is a top perspective view of a portion of an example microfluidic chip having example anchored nano particle assemblies.
Figure 11:
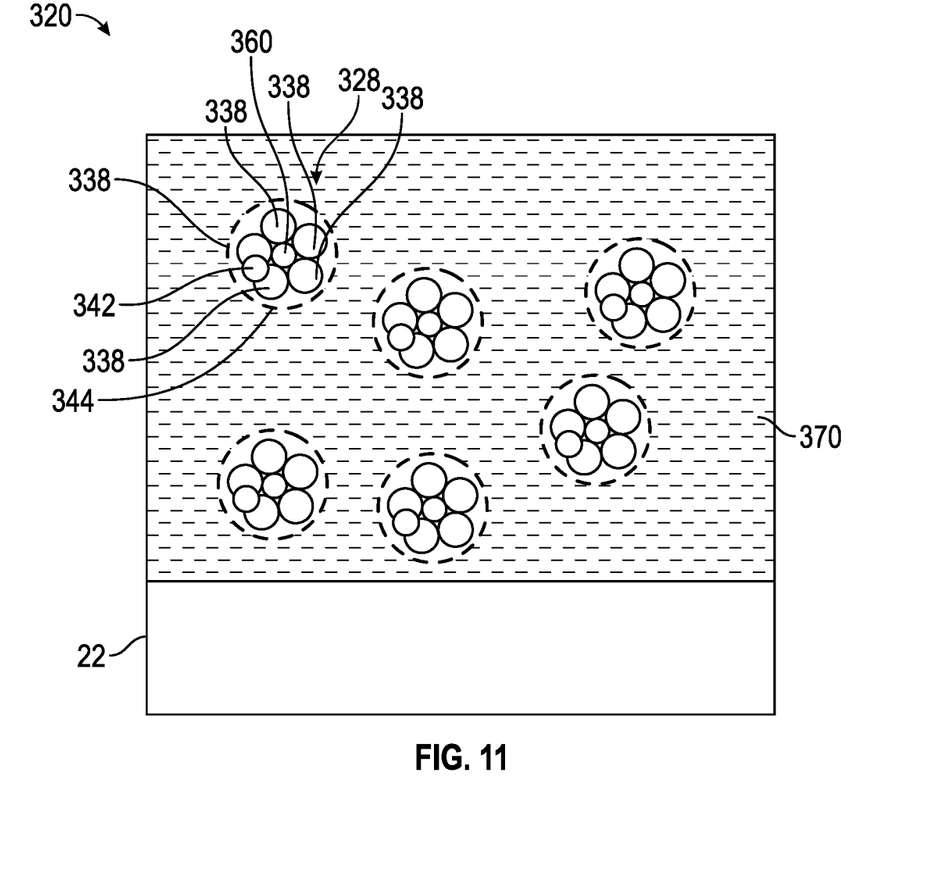
FIG. 11 is a sectional view illustrating portions of the example microfluidic chip of FIG. 10 following dis-anchoring of the example spectroscopic nano particle assemblies in fluid.

FIGS. 10 and 11 illustrate portions of another example microfluidic chip 320, an example implementation of microfluidic chip 20 described above. FIG. 10 illustrates microfluidic chip 320 in a stored state, during which nano particle assemblies 328 are anchored by a sacrificial layer 352 and while chamber 24 is devoid of fluid. FIG. 11 illustrates use of microfluidic chip 320 in which nano particle assemblies 328 are dis-anchored and are suspended in a fluid 370.

Each nano particle assembly 328 comprises a cluster or grouping of individual nanoparticles 338 providing plasmonically active surfaces. The plasmonic active surfaces may comprise a metal. For example, the plasmonically active surfaces of the individual particles may comprise noble metals, such as ruthenium (Ru), rhodium (Rh), palladium (Pd), silver (Ag), osmium (Os), iridium (Ir), platinum (Pt), and gold (Au), as well as copper, or alloys thereof. Other metals may be used provide the plasmonic surfaces, such as aluminum (Al), titanium (Ti), or other metals.

Although each assembly 328 is illustrated as comprising five adjacent nanoparticles 338, in other implementations, each assembly 328 may comprise other numbers of nanoparticles assembled or held adjacent to one another. For example, assembly 328 may comprise a dimer, trimer or tetramer. Junctions between the nanoparticles of the assembly 328 form at least one "hot spot".

Each nano particle assembly 328 further comprises at least one reporter molecule 360 (sometimes referred to as a spectroscopic tagging molecule) may be captured or trapped in the junctions, wherein the reporter molecule 360 emits a signature radiation pattern, which is enhanced as a result of the molecule being captured in the hotspot. The reporter molecules 360 may be any number of molecules that give a spectroscopic response, for example, in a surface enhanced luminescence technique. For use in SERS, the reporter molecule may be trans-1,2-bis (4-pyridyl) ethylene. However, any number of other reporter molecules 360 may be used depending on the spectroscopic techniques.

In the example illustrated, each nano particle assembly 328 is additionally functionalized using functionalizing molecules 342 with the binding agent on one end and a functional group on the other end. For example, the binding agent may include thiols for binding to the exposed portion of the plasmonic surface of the assembly 328. In one implementation, the functionalizing molecules 342 are adhered to nano particle assembly 328 after nano particle assembly 328 have been dis-anchored and are suspended in fluid 370 as shown in FIG. 11. In other implementations, the functionalizing module 342 are provided as part of each nano particle assembly 328 prior to the nano particle assembly 328 being dis-anchored.

The functional group may be designed to promote stability in solution, bind to specific substrates or tissues, or both. Multiple functionalization molecules can also be utilized. One example of a functional group may be a monoclonal antibody selected to bind to an express group on the surface of a cell. The functional group may comprise a short DNA segment that is to bind to a complementary DNA segment. A functional group may comprise a long paraffinic chain that stabilizes the nano particle assembly 328 in organic materials, such as solvents, fatty acids, triglycerides and the like.

In some implementations, the functional group may be a therapeutic agent. For example, therapeutic agent may be released when the nano particle assembly 328 is exposed to an excitation source. In such an implementation, the functional group may facilitate the delivery of local therapeutics with a plasmonic the activated drug delivery system using nano particle assembly 328.

In some implementations, nano particle assembly 328 may be tuned to specific applications. For example, in some implementations, the size and/or geometry of nano particle assembly 328 may be customized for a particular application such as where the nano particle assembly 328 is intended to bind to a particular substrate or tissue, where the nano particle assembly 328 is to pass through cell walls or where the nano particle assembly 328 is to be utilized in solution.

In some implementations, the nano particle assembly 328 may be encapsulated or covered with a protective outer coating 344 (shown by broken lines) that may protect any reporter molecules or stabilize the assembly 328 in solution. For example, the protective coating may promote stability of a suspension or block further aggregation of the nano particle assembly 328. Examples of such a coating include, but are not limited to, silicon dioxide, metal oxides, metal carbides, metal sulfide, diamond, spinel structures ($MgAl_2O_4$) and the like. Protective coating may be applied using a vapor deposition technique, atomic layer deposition or liquid deposition techniques.

Sacrificial layer 352 comprises a layer of material that anchors nano particle assemblies 328 within chamber 24. Sacrificial layer 352 comprises a layer on the internal surface of chamber 24 and which at least partially encapsulates nano particle assembly 328. In one implementation, sacrificial layer 352 has a chemical composition and thickness or dimension such that sacrificial layer 352 breaks down or dissolves upon exposure to the fluid having a predetermined chemical composition, releasing or dis-anchoring nano particle assembly 328 into the fluid 370. For example, in one implementation, sacrificial layer 352 may comprise an aluminum oxide material or PMMA. Examples of other sacrificial materials that may be utilized, depending upon the fluid utilized to dis-anchor the nano particle assembly 328, include, but are not limited to, titanium, chromium, polyimide, poly(methyl methacrylate) or polystyrene.

In other implementations, sacrificial layer 352 has a chemical composition and thickness or dimension such that the sacrificial layer 352 breaks down and releases nano particle assembly 328 in response to other applied stimulus or excitation. For example, in one implementation, sacrificial layer 352 has a chemical composition and thickness such that a breakdown in response to reaching a predetermined temperature or in response to applied electromagnetic radiation in the form of certain optical wavelengths. In such an implementation, the stimulus may be applied while in the fluid such that the released nano particle assemblies 328 become suspended in the fluid 370. Examples of such sacrificial materials for layer 352, include, but are not limited to, poly(methyl methacrylate), polyimide or polystyrene.

Figure 12:
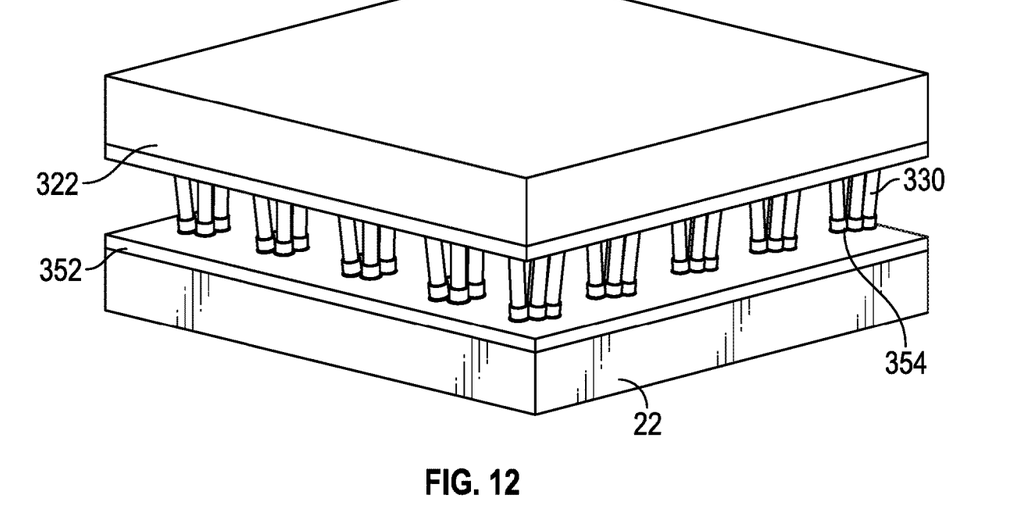
FIG. 12 is a perspective view illustrating the embedding of the metallic caps and reporter molecules of closed nano pillars into a sacrificial layer.
Figure 13:
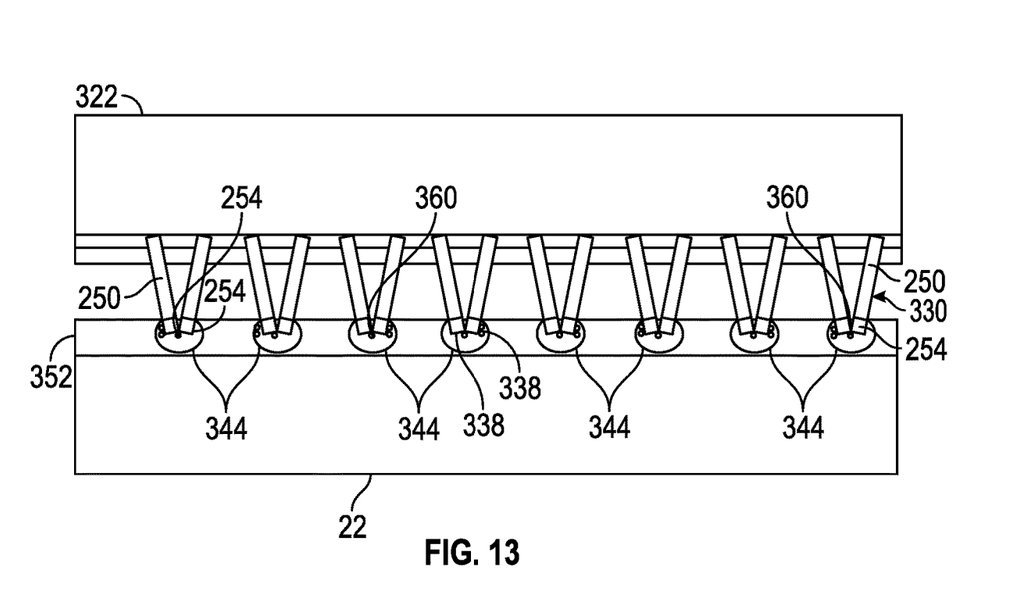
FIG. 13 is a sectional view illustrating the embedding of the metallic caps and reporter molecules of the closed nano pillars into the sacrificial layer.
Figure 14:
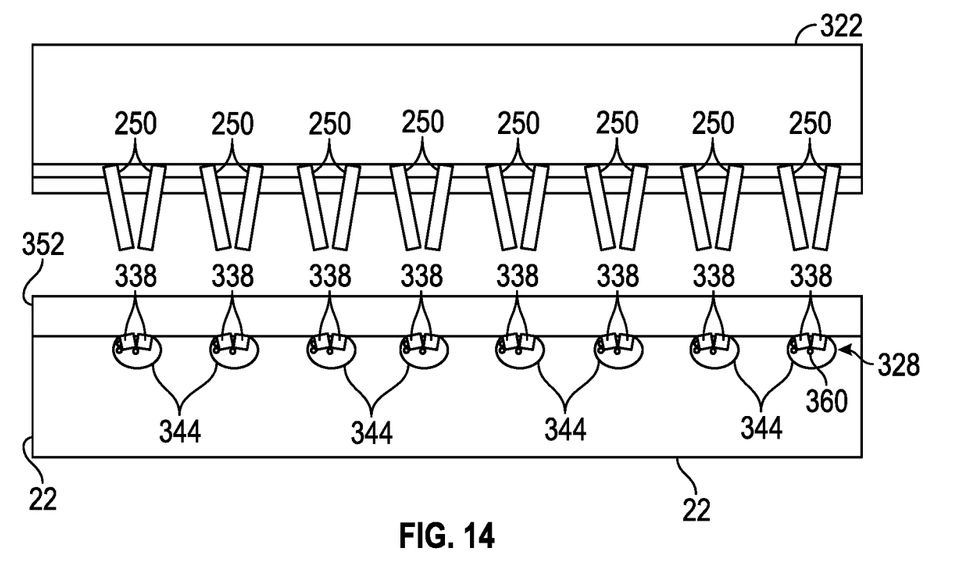
FIG. 14 is a sectional view illustrating separation of posts of the nano pillars, leaving the spectroscopic nano particle assemblies of FIG. 10 embedded in the sacrificial layer.

FIGS. 12-14 illustrate one example method for forming those portions of microfluidic chip 320 illustrated in FIG. 10. As shown by FIGS. 12 and 13, nano pillars 330 are formed on a platform 322. Nano pillars 330 are similar to nano pillars 230 described above and are formed in a similar fashion except the nano pillars 330, in some implementations, may omit sacrificial layer 252 and sacrificial layer 254, wherein metallic caps 254 are formed directly upon posts 250. The nano pillars 330 may be closed and the reporter molecules 360 may be adhered to the closed nano pillars 330 in the same fashion as described above with respect to FIGS. 8 and 9.

As further shown by FIGS. 12 and 13, platform 322 and the closed nano pillars 330, along with the captured reporter molecules 360, are inverted opposite to substrate 22 and its overlying layer 352 of sacrificial material. The collapsed groups of nano pillars 330 are pressed into the sacrificial layer 352, which is fluid. For example, in one implementation, sacrificial layer 352 may be heated to a softened or molten state. The collapsed groups of nano pillars 330 are left in place while the sacrificial layer 352 cools and hardens.

As shown by FIG. 14, Once the sacrificial layer 352 has hardened, the platform 322 and the retained posts 250 may be removed. The removal of the platform 322 may break or disconnect the posts 250 from the metal caps 354, leaving the metal caps 354 forming nanoparticles 338 and the adhered reporter molecules 360 embedded in the sacrificial layer 352 as a nano particle assemblies 328.

Figure 15:
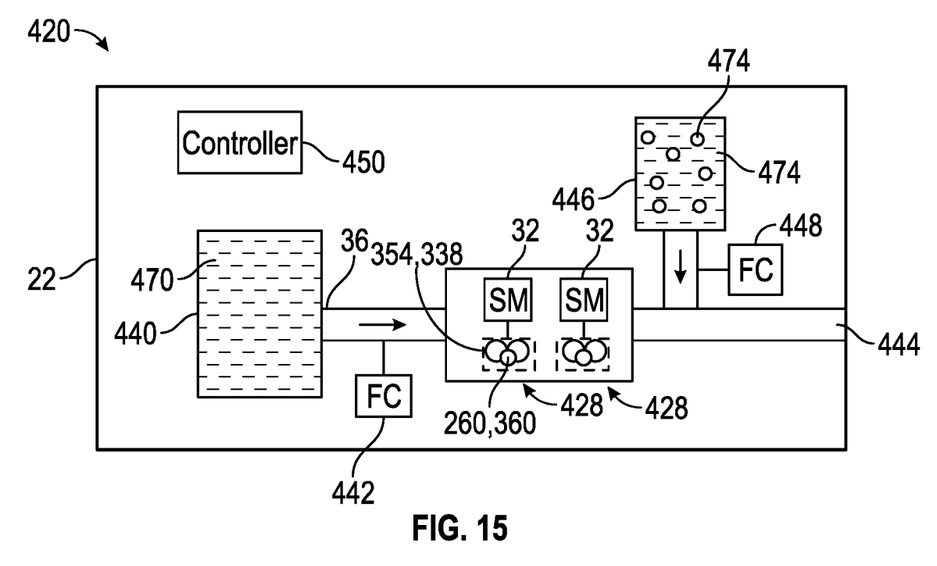
FIG. 15 is a schematic diagram of an example microfluidic chip having anchored spectroscopic nano particle assemblies.

FIG. 15 schematically illustrates portions of an example microfluidic chip 420. Microfluidic chip 420 comprises substrate 22, microfluidic chamber 24, spectroscopically active nano particle assemblies 428, sacrificial material 32, fluid supply port 36, fluid reservoir 440, flow controller 442, discharge passage 444, reagent reservoir 446, flow controller 448 and controller 450. Substrate 22, chamber 24 and supply port 36 are described above.

Nano particle assemblies 428 are each similar to either nano particle assembly 228 or nano particle assembly 328 described above except that nano particle assembly 428 is not functionalized. Nano particle assemblies 428 each have at least one captured reporter molecule 260, 360 as described above. In one implementation, each nano particle assembly 428 is anchored in a fashion similar to the anchoring of nano particle assemblies 228 by posts 250 and sacrificial layer or 252 described above with respect to FIG. 5. In another implementation, nano particles assemblies 428 are anchored in a fashion similar to the anchoring of nano particle assemblies 328 by sacrificial layer 352 as described above with respect to FIG. 10. Each nano particle assembly 428 may comprise any of a number of nano particles formed by metallic caps as described above. Although microfluidic chip 420 is illustrated as having a pair nano particle assembly 428 anchored within chamber 24 for ease of illustration, it should be appreciated that chamber 24 may contain a greater number of nano particle assemblies 428 anchored within chamber 24.

Fluid reservoir 440 comprises a chamber containing fluid for the entrainment or suspension of nano particle assemblies 428, once this anchored or released. In one implementation, fluid reservoir 440 contains a fluid 470 that breaks down her dissolves sacrificial material 32 to dis-anchor release nano particle assemblies 428. For example, fluid 470 may comprise a weak acid or base so as to release the nano particle assembly 428 into solution. In one implementation, sacrificial layer may be formed from Poly(methyl methacrylate) (PMMA), also known as acrylic or acrylic glass, wherein the sacrificial material 32 is dissolvable in a fluid 470 such as acetone.

Flow controller 442 comprises a device that controls the flow of fluid 470 out of reservoir 440 into chamber 24. In one implementation, flow controller 442 may comprise a pump. For example, in one implementation, flow controller 442 may comprise an inertial pump formed by a fluid actuator. Fluid actuators that may be implemented as inertial pumps described herein may include, for example, thermal actuators, piezo-membrane based actuators, electrostatic membrane actuators, mechanical/impact driven membrane actuators, magnetostrictive drive actuators, electrochemical actuators, other such microdevices, or any combination thereof. In some examples, fluid actuators may be formed in microfluidic channels by performing various microfabrication processes.

In some examples, a fluid actuator may correspond to an inertial pump. As used herein, an inertial pump corresponds to a fluid actuator and related components disposed in an asymmetric position in a microfluidic channel, where an asymmetric position of the fluid actuator corresponds to the fluid actuator being positioned less distance from a first end of a microfluidic channel as compared to a distance to a second end of the microfluidic channel. Accordingly, in some examples, a fluid actuator of an inertial pump is not positioned at a mid-point of a microfluidic channel. The asymmetric positioning of the fluid actuator in the microfluidic channel facilitates an asymmetric response in fluid proximate the fluid actuator that results in fluid displacement when the fluid actuator is actuated. Repeated actuation of the fluid actuator causes a pulse-like flow of fluid through the microfluidic channel.

In some examples, an inertial pump includes a thermal actuator having a heating element (e.g., a thermal resistor) that may be heated to cause a vapor bubble to form in a fluid proximate the heating element. In such examples, a surface of a heating element (having a surface area) may be proximate to a surface of a microfluidic channel in which the heating element is disposed such that fluid in the microfluidic channel may thermally interact with the heating element. In some examples, the heating element may comprise a thermal resistor with at least one passivation layer disposed on a heating surface such that fluid to be heated may contact a topmost surface of the at least one passivation layer. Formation and subsequent collapse of such vapor bubble may generate circulation flow of the fluid. As will be appreciated, asymmetries of the expansion-collapse cycle for a bubble may generate such flow for fluid pumping, where such pumping may be referred to as "inertial pumping." In other examples, a fluid actuator corresponding to an inertial pump may comprise a membrane (such as a piezoelectric membrane) that may generate compressive and tensile fluid displacements to thereby cause fluid flow.

In another implementation, flow controller 442 may comprise a microfluidic valve. For example, in one implementation, flow controller 442 may comprise a constriction that forms a capillary break, wherein the capillary break may be broken by the displacement of fluid caused by fluid actuator such as described above. In some implementations, flow controller 442 may comprise a film or membrane that may be punctured, torn or otherwise broken to allow fluid to flow from reservoir 440 into chamber 24, dis-anchoring nano particle assemblies 428.

Discharge passage 444 comprises a microfluidic passage extending from chamber 24. Discharge passage 444 directs a flow of fluid carrying the nano particle assemblies 428.

Reagent reservoir 446 comprises a chamber containing a fluid 474 carrying reagent molecules 476. Reagent molecules 476 may comprise functionalizing molecules similar to functionalizing molecules 342 described above.

Flow controller 448 is similar to flow controller 442 described above except that flow controller 448 controls the flow of fluid 474 and reagent molecules 476 to discharge passage 444. In other implementations, flow controller 448 may control the flow of fluid 474 and reagent molecules 476 into chamber 24. Flow controller 448 facilitate the selective addition of reagent molecules 476 to the dis-anchored nano particle assemblies 428.

Controller 450 facilitates the automated preparation of a solution containing spectroscopically active nano particle assemblies. Controller 450 may comprise a processing unit and associated instructions stored on a non-transitory computer-readable medium or may comprise an integrated circuit having logic or logic elements. Controller 450 outputs control signals controlling flow controllers 442 and 448 to control the preparation of the solution and the dis-anchored nano particle assemblies 428. For example, controller 450 may output first control signals causing flow controller 442 to supply fluid from reservoir 470 to chamber 24, dis-anchoring nano particle assemblies 428. Thereafter, controller 450 may output second control signals causing flow controller 448 to supply fluid 474 and reagent molecules 476 to the dis-anchored nano particle assemblies 428 which are discharged through discharge passage 444.

Figure 16:
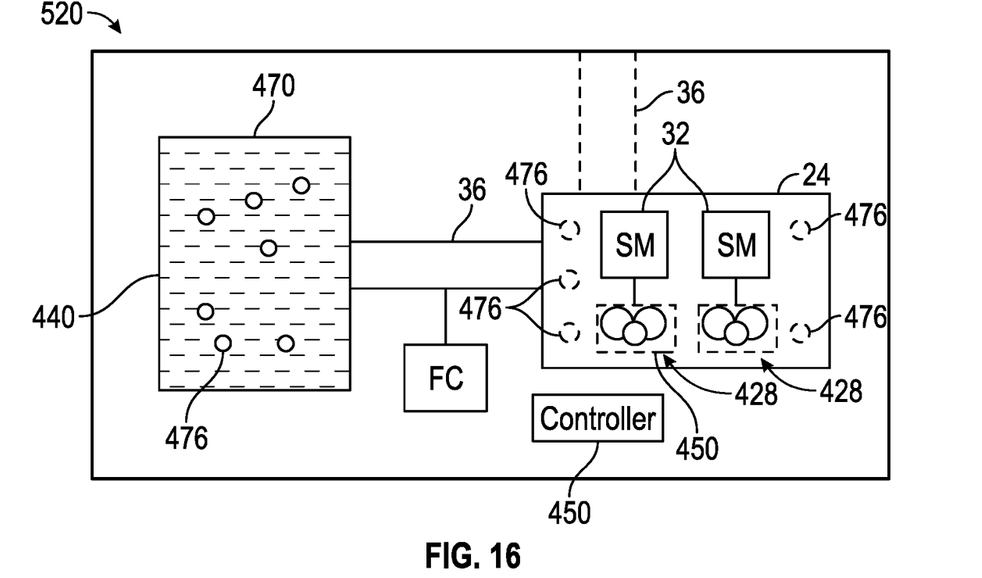
FIG. 16 is a schematic diagram of an example microfluidic chip having anchored spectroscopic nano particle assemblies.

FIG. 16 schematically illustrates portions of an example microfluidic chip 520. Microfluidic chip 520 is similar to microfluidic chip 420 except that microfluidic chip 520 omits reservoir 446 and flow controller 448, providing reagent molecules 476 in fluid 470 and/or within chamber 24 as freeze-dried molecules. Those remaining components of microfluidic chip 520 which correspond to components of microfluidic chip 420 are numbered similarly.

As shown by FIG. 16, fluid reservoir 440 contains a fluid 470 in which reagent molecules 476 (described above) are carried. In response to signals from controller 450, flow controller 442 supplies fluid 470 and reagent molecules 476 to chamber 24, wherein nano particle assemblies 428 are dis-anchored and wherein reagent molecules 476, such as functionalizing molecules, may join or otherwise adhere to nano particle assemblies 428. As shown by broken lines, in other implementations, microfluidic chip 520 may omit reservoir 440, wherein microfluidic chip 520 comprises an external fluid supply port 36' through which fluid 470 and reagent modules 476 may be supplied. In some implementations, fluid 470 may omit reagent molecules 476, where reagent molecules 476, freeze-dried within chamber 24, are sufficient to functionalize the nano particle assemblies 428. In some implementations, the freeze-dried reagent molecules 476 within chamber 24 may be omitted.

Figure 17:
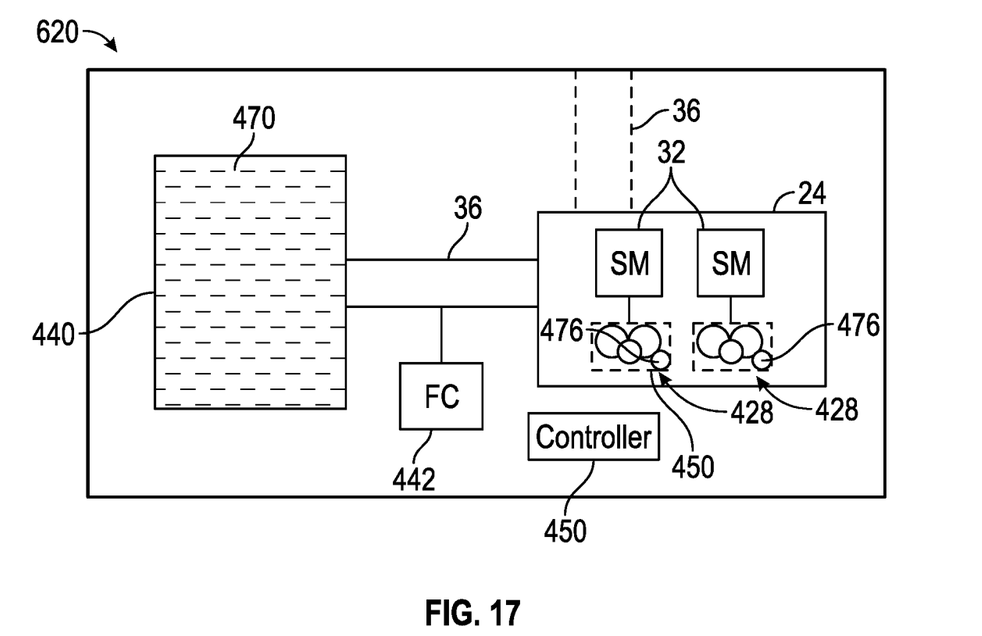
FIG. 17 is a schematic diagram of an example microfluidic chip having anchored spectroscopic nano particle assemblies.

FIG. 17 schematically illustrates portions of an example microfluidic chip 620. Microfluidic chip 620 is similar to microfluidic chip 520 except that fluid 470 in reservoir 440 omits reagent molecules 476, wherein reagent models 476 are pre-attached to nano particle assemblies 428 and chamber 24 while nano particle assemblies 428 are anchored within chamber 24. In such an implementation, the metal caps that form nano particles 354, 338 may be functionalized while the nano particles are supported by post 250 before closure of the nano pillars.

Figure 18:
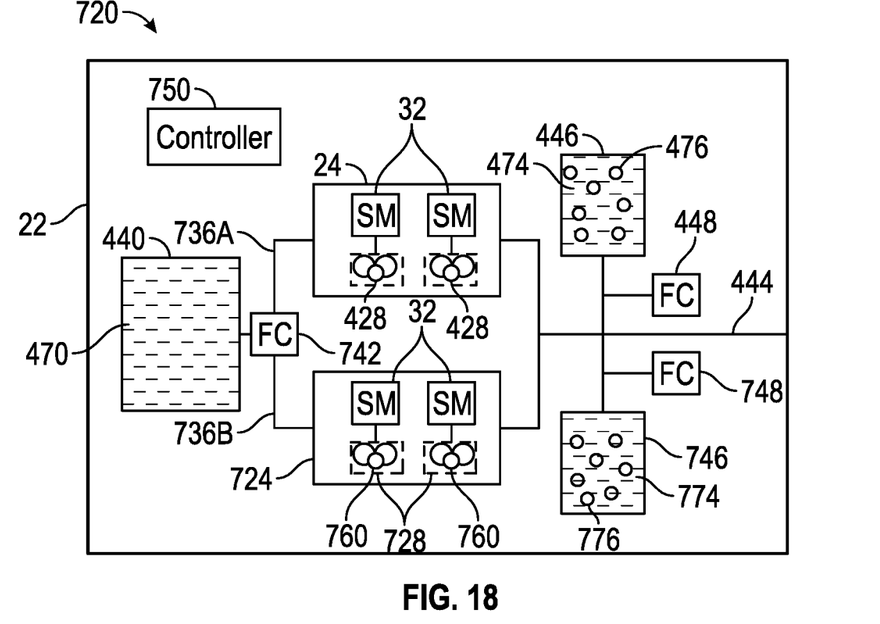
FIG. 18 is a schematic diagram of an example microfluidic chip having anchored spectroscopic nano particle assemblies.

FIG. 18 schematically illustrates portions of an example microfluidic chip 720. Microfluidic chip 720 provides automated preparation of a customized spectroscopic tagging solution. Microfluidic chip 720 is similar to microfluidic chip 420 described above except that microfluidic chip 720 additionally comprises chamber 724, nano particle assemblies 728, fluid controller 742, reagent reservoir 746 and fluid controller 748. Those remaining components of microfluidic chip 720 which correspond to components of microfluidic chip 420 are numbered similarly.

Chamber 724 is similar to chamber 24. Chamber 724 is formed in substrate 22 and contains nano particle assemblies 728. Chamber 724 is devoid of fluid.

Nano particle assemblies 728 are similar to nano particle assemblies 428 except that nano particle assembly 728 comprise reporter molecules 760 which are different than reporter molecule 260, 360 of nano particle assemblies 428. As with nano particle assemblies 428, nano particle assemblies 728 are anchored within chamber 724 by sacrificial material 32. In some implementations, nano particle assemblies 728 may be anchored in a fashion similar to that shown in FIG. 5. In another implementation, nano particle assemblies 728 may be anchored in a fashion similar to that described above with respect to FIG. 10.

Fluid controller 742 selectively directs fluid 470 from reservoir 4402 one or both of chambers 24, 724. In one implementation, controller 742 comprises a valve. In one implementation, fluid controller 742 may comprise a pair of inertial fluid pumps that may be selectively actuated to direct fluid through microfluidic passage 736A to chamber 24 and/or through microfluidic passage 736B to fluid chamber 724.

Reservoir 746 is similar to reservoir 446 except that reservoir 746 contains fluid 774 in which reagent molecules 776 are suspended or carried. Reagent molecules 776 are different than reagent molecules 476 contained in reservoir 446. For example, reagent molecules 776 may comprise functionalizing molecules having different functionalizing properties as compared to those of molecules 476.

Flow controller 748 is similar to flow controller 448 described above except that flow controller 748 selectively controls the flow of fluid from reservoir 746 to discharge passage 444. Controller 750 facilitates the automated preparation of a customized solution containing spectroscopically active nano particle assemblies. Controller 750 may comprise a processing unit and associated instructions stored on a non-transitory computer-readable medium or may comprise an integrated circuit having logic or logic elements. Controller 750 outputs control signals controlling flow controllers 742, 448 and 748 to control the preparation of the spectroscopic tagging solution. Controller 750 facilitates the preparation of any one of at least four different spectroscopic tagging solutions. For example, controller 750 may output control signals to flow controller 742, 448 and 748 so as to provide a solution comprising nano particle assemblies 428 functionalized with functionalizing molecules 476, nano particle assemblies 428 functionalized with functionalizing molecules 776, nano particle assemblies 728 functionalized with functionalizing molecules 476 or nano particle assemblies 728 functionalized with functionalizing molecules 776. Such selection may be made via a user input, such as a keyboard, mouse, and the like, in communication with controller 750.

Figure 19:
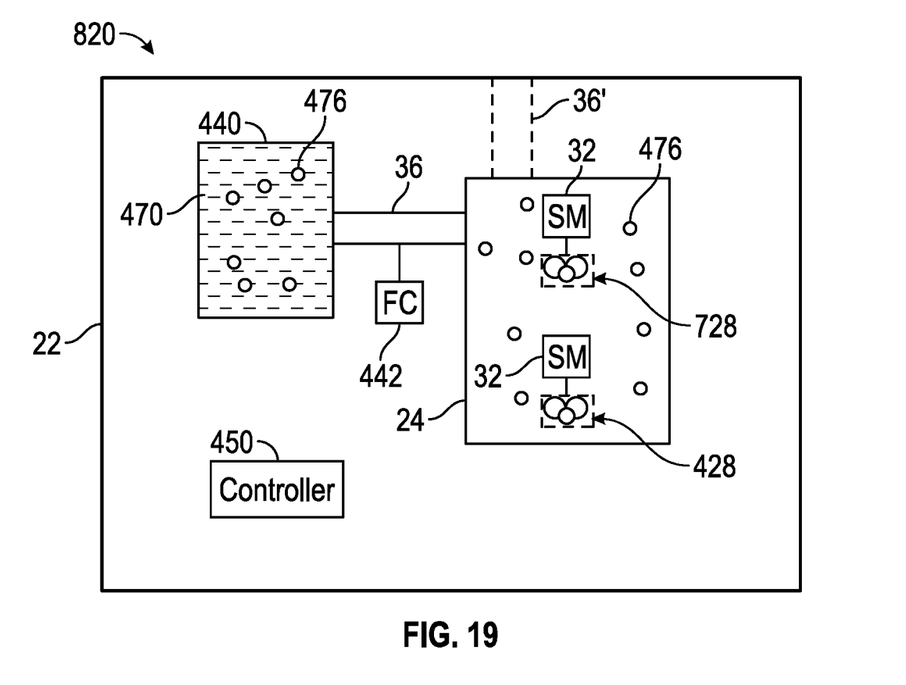
FIG. 19 is a schematic diagram of an example microfluidic chip having anchored spectroscopic nano particle assemblies.

FIG. 19 schematically illustrates portions of an example microfluidic chip 820. Microfluidic chip 820 is similar to microfluidic chip 520 described above except that chamber 24 contains different anchored nano particle assemblies 428 and 728. In one implementation, nano particle assembly 428 and 728 are separately formed (such as described above with respect to FIGS. 7-9 or FIGS. 12-14, wherein the different nano particle assemblies 428, 728 are mounted within chamber 24.

In response to signals from controller 450, flow controller 442 supplies fluid 470, with functionalizing molecules 476, to chamber 24. As a result, nano particle assemblies 428, 728 are dis-anchored or released into fluid 470 and are also functionalized. The resulting solution contains two different types of nano particle assemblies 428, 728, functionalized with functionalizing molecules 476.

Although the present disclosure has been described with reference to example implementations, workers skilled in the art will recognize that changes may be made in form and detail without departing from the spirit and scope of the claimed subject matter. For example, although different example implementations may have been described as including one or more features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. A microfluidic chip comprising:
   a substrate;
   a chamber supported by the substrate;
   a sacrificial material in the chamber;
   a spectroscopically active nano particle assembly anchored within the chamber by the sacrificial material, each spectroscopically active nano particle assembly comprising a cluster of nanoparticles;
   a fluid supply port connected to the chamber; and
   a microfluidic channel within the substrate leading to the fluid supply port, the microfluidic channel having a millimeter sized scale or smaller scale.

2. The microfluidic chip of claim 1 further comprising a reagent supply to supply a reagent to the spectroscopically active nano particle assembly.

3. The microfluidic chip of claim 2 further comprising a second reagent supply to supply a second reagent, different than the reagent, to the spectroscopically active nano particle assembly.

4. The microfluidic chip of claim 1 further comprising a second spectroscopically active nano particle assembly anchored within the chamber by the sacrificial material.

5. The microfluidic chip of claim 4, wherein the spectroscopically active nano particle assembly comprises a first reporter molecule and wherein the second spectroscopically active nano particle assembly comprises a second reporter molecule different than the first reporter molecule.

6. The microfluidic chip of claim 4 comprising a continuous layer of the sacrificial material, the continuous layer of the sacrificial material anchoring the spectroscopically active nano particle assembly and the second spectroscopically active nano particle assembly.

7. The microfluidic chip of claim 1 further comprising:
   a first flexible post releasably supporting a first plasmonic cap forming a first portion of the spectroscopically active nano particle assembly; and
   a second flexible post releasably supporting a second plasmonic cap forming a second portion of the spectroscopically active nano particle assembly, wherein the second flexible post is bent towards the first flexible post to locate the first plasmonic cap adjacent the second plasmonic cap.

8. The microfluidic chip of claim 7 further comprising:
a first sacrificial layer between the first flexible post and the first plasmonic cap; and
a second sacrificial layer between the second flexible post and the second plasmonic cap.

9. The microfluidic chip of claim 1, wherein the spectroscopy active nano particle assembly comprises a reporter molecule.

10. The microfluidic chip of claim 1, wherein the nano particle assembly comprises at least one protective coating comprising silicon dioxide, metal oxides, metal nitrides, metal carbides or combinations thereof.

11. The microfluidic chip of claim 1, wherein the chamber is devoid of fluid.

12. The microfluidic chip of claim 11 further comprising:
a fluid reservoir connected to the fluid supply port and containing a fluid, the fluid supply port being closed to inhibit flow of the fluid into the chamber, wherein the fluid supply port is selectively openable to permit flow of the fluid into the chamber.

13. The microfluidic chip of claim 1, wherein the microfluidic channel has no greater than a micrometer sized scale.

14. The microfluidic chip of claim 1, further comprising:
a second microfluidic channel in the substrate and extending from the chamber; and
a third microfluidic channel in the substrate directly connected to an intermediate location of the second microfluidic channel, downstream from the chamber, to mix fluid supplied through the third microfluidic channel with fluid discharged from the chamber and moving through the second microfluidic channel.

15. The microfluidic chip of claim 1 further comprising a flow controller on the chip to control flow of fluid within the substrate with respect to the chamber.

16. The microfluidic chip of claim 15, wherein the flow controller is selected from a group of fluid controllers consisting of: an inertial pump and a microfluidic valve.

17. The microfluidic chip of claim 15, wherein the flow controller comprises a first inertial pump on the substrate to move fluid through the microfluidic channel, the microfluidic chip further comprising:
a second microfluidic channel in the substrate; and
a second inertial pump on the substrate to move fluid through the second microfluidic channel.

18. The microfluidic chip of claim 1 further comprising a fluid reservoir in the substrate.

19. A microfluidic chip comprising:
a substrate;
a chamber in the substrate;
a layer of sacrificial material in the chamber;
spectroscopically active nano particle assemblies anchored by the layer within the chamber;
a solvent supply passage in the substrate and connected to the chamber;
a discharge passage in the substrate and extending from the chamber; and
a reagent supply passage in the substrate and connected to the discharge passage.

20. A microfluidic chip comprising:
a substrate;
a chamber supported by the substrate;
a sacrificial material in the chamber;
a spectroscopically active nano particle assembly anchored within the chamber by the sacrificial material, each spectroscopically active nano particle assembly comprising a cluster of nanoparticles;
a fluid supply port connected to the chamber; and
a fluid reservoir connected to the fluid supply port and containing a fluid, the fluid supply port being closed to inhibit flow of the fluid into the chamber, wherein the fluid supply port is selectively openable to permit flow of the fluid into the chamber.

* * * * *